United States Patent [19]

Love

[11] Patent Number: 5,509,930
[45] Date of Patent: Apr. 23, 1996

[54] STENTLESS HEART VALVE

[75] Inventor: Jack W. Love, Santa Barbara, Calif.

[73] Assignee: Autogenics, Newbury Park, Calif.

[21] Appl. No.: 170,002

[22] Filed: Dec. 17, 1993

[51] Int. Cl.$^6$ .................................. A61F 2/24; A61F 2/76
[52] U.S. Cl. ................................................. 623/2; 623/900
[58] Field of Search .................................. 623/2, 66, 900

[56] References Cited

U.S. PATENT DOCUMENTS

| | | |
|---|---|---|
| 3,655,306 | 4/1972 | Ross et al. . |
| 3,686,740 | 8/1972 | Shiley . |
| 4,079,468 | 3/1978 | Liotta et al. ............................ 623/900 |
| 4,172,295 | 10/1979 | Batten ......................................... 623/2 |
| 4,218,782 | 8/1980 | Rygg ........................................... 623/2 |
| 4,470,157 | 9/1984 | Love ........................................... 623/2 |
| 4,629,459 | 12/1986 | Ionescu et al. ............................ 623/2 |
| 4,790,844 | 12/1988 | Ovil . |
| 4,960,424 | 10/1990 | Grooters . |
| 5,197,979 | 3/1993 | Quintero et al. . |
| 5,215,541 | 6/1993 | Nashef et al. ............................ 8/94.11 |

OTHER PUBLICATIONS

J. C. R. Lincoln et al., "Pulmonary Valve Replacement with Fascia Lata", reprint from The Annals of Thoracic Surgery, vol. 13, No. 2, Feb. 1972.

P. Casabona et al., "Stentless Porcine and Pericardial Valve in Aortic Position", Twenty-Eight Annual Meeting of the Society of Thoracic Surgeons, Orlando, Florida, Feb. 3–5, 1992.

Ing-Sh Chiu et al., "Fate of the Autologous Tri-Cusp-–Valved Pericardial Conduit in the Right Ventricular Outflow Tract of Growing Pigs", Proceedings of the National Science Council, ROC, Part B: Life Sciences, vol. 16, No. 1, 1992, pp. 23–30.

*Primary Examiner*—David Isabella
*Assistant Examiner*—Laura Fossum
*Attorney, Agent, or Firm*—Knobbe, Martens, Olson & Bear

[57] ABSTRACT

A stentless heart valve assembled from autologous tissue is provided. The tissue is cut into a rectangular shape, folded, and stapled at several locations to form the cusps of the valve. The outer walls of the valve are pinched at the midpoint of each cusp to prevent the cusps from adhering to the valve walls. The ends of the rectangle are then stapled to form the annular valve itself.

30 Claims, 3 Drawing Sheets

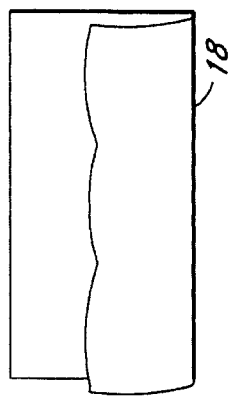
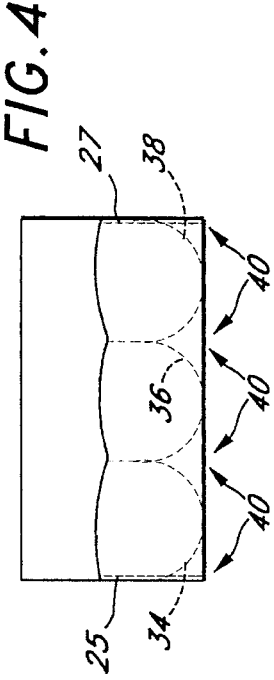
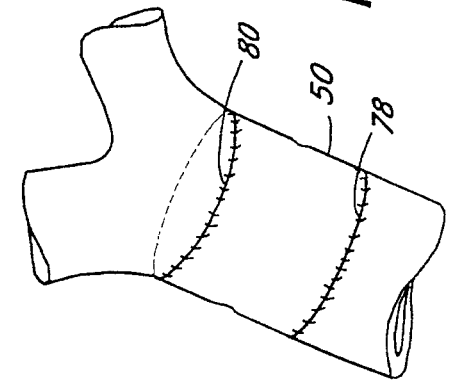
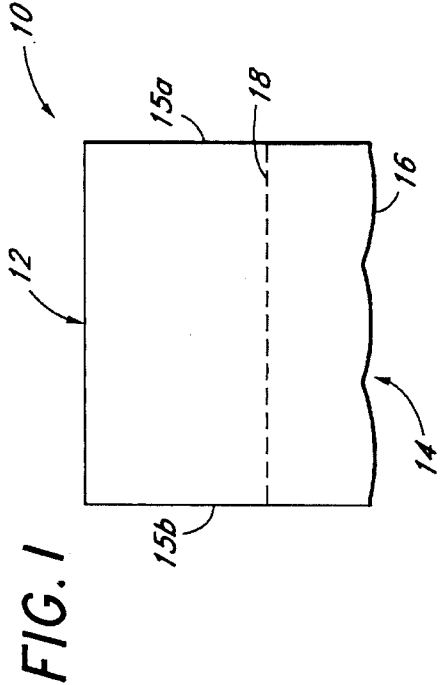
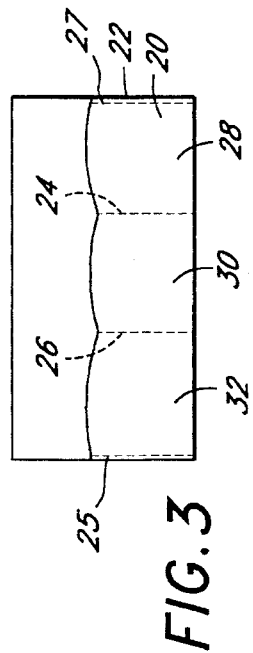
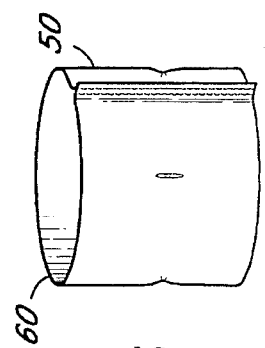

STENTLESS HEART VALVE

BACKGROUND OF THE INVENTION

The present invention relates to heart valve replacements. Replacements are required for patients whose own valves have begun to fail. While many heart valve replacements rely on combinations of tissue and mechanical elements, the creation of valves from tissue, including autologous tissue, without the use of a supporting assembly or stent is also known. Senning, for example, describes such a technique for replacing a diseased heart valve with one made from the patient's own tissue in the Journal of Thoracic and Cardiovascular Surgery at Vol. 54, p. 465–470 (1967). Senning employed a piece of the patient's untreated fascia lata to fashion a trileaflet valve and sutured the new valve to the patient's native valve remnant with a continuous suture, reinforced at the valve's commissures with pledgeted sutures.

While Senning and other surgeons recorded some notable successes with their stentless autologous-tissue heart valves, they quickly encountered several difficulties. These included shrinkage and calcification of the tissue comprising the replacement valve. Additionally, fabrication of autologous-tissue valves during cardiac surgery required great skill and could not be done rapidly. Consequently, the technique of using autologous tissue to fashion stentless heart valves was soon abandoned by most surgeons in favor of the use of glutaraldehyde-tanned, stent-mounted valves, or mechanical prostheses.

Exemplary embodiments of such bioprostheses are disclosed and claimed in U.S. Pat. No. 4,470,157 and 5,163,955 assigned to Autogenics, assignee of this application, which uses stent assemblies to support a piece of autologous tissue.

SUMMARY OF THE INVENTION

The heart valve of the present invention is a self-supporting stentless prosthetic heart valve preferably formed during open heart surgery from autologous pericardium, removed from the patient during the surgical procedure. The only operations required to construct the heart valve are cutting to a precise geometry, folding, and securing the tissue together with staples or other fastening means. During surgery, the patient's diseased valve is excised and the annulus of the valve is measured. The tissue used to construct the valve is then cut from the patient with the aid of a template.

The heart valve replacement of the present invention is constructed from a single piece of autologous tissue treated by brief immersion in a weak glutaraldehyde solution. Brief immersion of the tissue aids in preventing calcification of the valve after implantation. After brief immersion, the tissue is cut into the required shape, preferably by use of a size-specific cutting die. Size-specific components, such as the cutting die, are preferably provided in kit form. The provision of kits corresponding to each annulus size advantageously puts all the items required by the surgeon to perform the valve replacement within ready reach, thereby minimizing the time required for the surgery.

The valve itself is a self-supporting annular body of tissue having distal and proximal ends and end edges. The proximal end of the tissue is preferably cut into a plurality of scalloped portions, and the tissue is folded to form inner and outer layers or walls of tissue. The distal portion located above the top or distal end of the inner layer of tissue serves as an outflow duct, and can be tailored to fit more closely the individual patient's vascular anatomy.

The inner and outer layers of tissue are secured together by a first set of staples or other suitable fastening means along a plurality of lines extending distally from the folded, proximal end of the tissue. This first set of staples forms a series of segments or pockets which form the leaflets of the valve. Next, the layers are again secured together by a second set of staples or other fastening means along the bottom of each of the segments in a series of arcs tangent at their midpoints to the fold. This second set of staples advantageously removes areas of bloodflow stagnation which would otherwise form during operation of the valve in the corners of each of the segments or pockets.

The valve maker then staples or otherwise secures the end edges of the tissue together to form the cylindrical body of the valve. The inner layers of tissue in each of the segments or pockets form each of the cusps of the completed valve. These cusps coapt with each other along three lines extending radially inward from the annulus of the valve.

The present invention advantageously prevents the cusps of the valve from adhering to the outer layer of tissue, by providing a staple or suture emplaced in the outer wall of the valve at a location midway along each segment wall opposite the distal end of the inner layer of tissue. In an alternative embodiment of the invention, this objective is achieved by securing a girdle around the midsection of the valve to form a sinus.

The stentless or self-supporting valve of the present invention is therefore quickly and easily, repeatably and accurately fabricated. The use of standardized, size-specific kits and a precise assembly technique advantageously allows the valve to be precisely fabricated in a matter of minutes during the open heart surgery procedure.

BRIEF DESCRIPTION OF THE DRAWINGS

FIG. 1 is a top view of a section of tissue used to construct the heart valve of the present invention.

FIG. 2 is a top view of the tissue section depicted in FIG. 1 after it has been folded.

FIG. 3 is a perspective view of the tissue section depicted in FIG. 2 illustrating the placement of the first longitudinal rows of staples.

FIG. 4 is a top view of the tissue section depicted in FIG. 3 illustrating the placement of the second row of staples in curvilinear geometry.

FIG. 5 is a perspective view of the valve constructed from the tissue section illustrated in FIG. 4.

FIG. 6 illustrates the implantation of a valve into the heart of a patient in the pulmonary outflow tract.

DETAILED DESCRIPTION OF THE PREFERRED EMBODIMENTS

Figure 7:
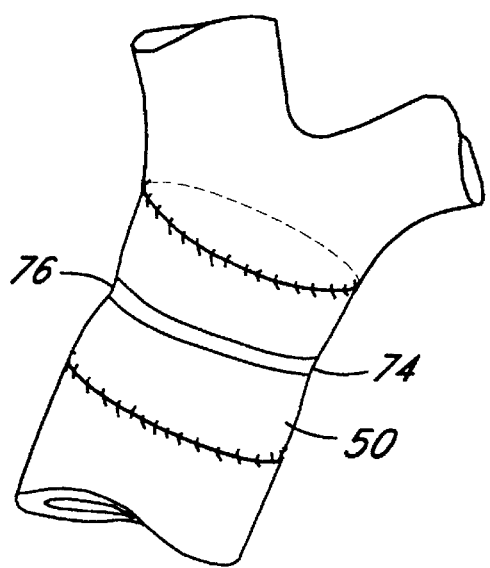
FIG. 7 is a schematic view of an implanted embodiment of the heart valve of the present invention, illustrating the placement of a girdle around the valve.

The self-supporting heart valve of the present invention is constructed from a single piece of tissue without the need for a supporting stent. The heart valve of the preferred embodiment of the present invention has three leaflets, formed from the piece of tissue and coapting between three commissures. The only operations required to construct the heart valve are cutting to precise geometry, folding, and securing the tissue together with staples or other fastening means.

As shown in FIG. 1, construction of the heart valve of the present invention begins with the cutting of a rectangular piece of tissue 10 having a proximal end 12 and a distal end 14 and end edges 15. The rectangular piece of tissue is preferably cut from a piece of the patient's pericardium obtained at the beginning of the open heart surgery, although other autologous, homologous, or heterologous tissue can be used. The pericardium is advantageously harvested by use of a roughly-sized template placed over the patient's pericardium to guide the surgeon in removing the tissue. Such a template is disclosed in U.S. Pat. No. 5,163,955 assigned to Autogenics, assignee of the present application. This patent is incorporated herein by reference.

The distal end 14 of the tissue piece 10 shown in FIG. 1 is advantageously cut with a scalloped edge 16, or it can be left straight-edged, as in the alternate embodiment of the invention depicted in FIGS. 9–12. Such a scalloped edge is preferred because it provides a larger amount of tissue along the edges of the valve leaflets where they coapt. The tissue piece 10 is preferably precisely cut into the proper shape by use of a size-specific cutting die. The size of the required tissue rectangle, and thus of the cutting die, is a function of the diameter of the valve to be replaced and the size of its adjacent inflow and outflow areas. In general, the length of the rectangle required for a valve having inner radius r is approximately $2\pi r$. The radius of the patient's valve is preferably determined by the use of a series of obturators inserted into the annulus by the surgeon. The obturators and their application in sizing the replacement valve are preferably similar to those disclosed in U.S. Pat. No. 5,163,955, assigned to Autogenics and application Ser. No. 08/169,618, filed Dec. 17, 1993, both of which are incorporated herein by reference. The width of the rectangle, i.e. the distance between the distal and proximal ends, is determined by the requirement that the valve leaflets be sufficiently long to coapt at the center of the tissue when it is formed into a cylinder. This consideration will be discussed below.

Dies suitable for cutting the tissue piece 10 are disclosed in the U.S. Pat. No. 5,163,955 and Application Ser. No. 08/169,620, filed Dec. 17, 1993, also assigned to Autogenics and which is incorporated herein by reference. The die (not shown) preferably has a plurality of knives mounted in a solid block of substrate, such as polycarbonate material, at locations corresponding to the desired edges of the tissue piece 10. The die is preferably provided as an element of a size-specific kit corresponding to the measured size of the valve annulus. The inclusion of the cutting die in a kit advantageously places it within easy reach of the surgeon during the assembly process. The cutting die advantageously includes an opposing surface against which the tissue is held during the cutting process. While the use of a cutting die to cut the tissue piece 10 to the desired shape is preferred, other means may also be used. These include providing a template having an outline of the areas to be cut and cutting the edges with a scalpel, using modified forceps, or laser-based or water jet systems.

The tissue 10 is preferably autologous tissue to prevent an adverse reaction from the patient's immune system. The preferred tissue is pericardium, since this tissue has been found to be satisfactory in practice, but other types of tissue, such as fascia lata or other autologous, homologous, or heterologous tissue, may also prove satisfactory. The tissue is preferably treated by brief immersion in a glutaraldehyde solution. Brief immersion accomplishes the two-fold purpose of making the tissue stiff enough to be used for valve construction in the operating room while preventing it from thickening, shrinking, and calcifying after it has been implanted as a heart valve prosthesis. The preferred glutaraldehyde concentration of the solution is approximately 0.6%, buffered to pH 7.4, since this strength has been found to render the tissue stiff enough for use in valve construction. The immersion time is preferably only a few minutes, typically 5 to 10 minutes, since long-duration immersion may promote calcification of tissue in the resulting valve. Other chemicals, such as glycerol, formaldehyde, or polyglycidyl ether, could also be used as fixing agents.

After being cut into the proper shape and briefly immersed, the tissue 10 is folded at a location 18 distal to its proximal end, as shown in FIG. 2. The fold forms an inner wall 20 and an outer wall 22, as is seen in FIG. 3. As described below, this inner wall 20 forms the valve leaflets. Consequently, the fold location 18 is chosen so that the inner wall 20 has a height sufficient for the valve cusps to completely close.

After folding the tissue 10, the valve maker applies sets of staples 24, 25, 26, and 27 to the inner and outer walls. The staples 24-27 extend distally from the folded location 18 and are parallel to the end edges of the tissue. These staples join the inner and outer surfaces 20 and 22 together along their height and segment the proximal portion of the tissue 10 into three segments 28, 30, and 32. The valve maker preferably adds three more sets of staples 34, 36, and 38 in a curvilinear pattern at the proximal end of the tissue. The curvilinear sets of staples should be tangent to the midpoint of each of the segments 28, 30, and 32 and their ends should not extend more than several millimeters above the fold location 16. The exact amount of extension required for the ends above the fold location 18 depends upon the size of the completed valve.

The sets 34, 36, and 38 of staples are advantageously added in the present invention to eliminate areas of stagnation in the blood flow through the valve and thus prevent the formation of blood clots in the valve. The curvilinear sets of staples achieve this objective by sealing off each of the segment corner areas 40, which would otherwise be the last areas to be purged of blood during the opening and closing of the valve.

The staple sets 24–27, 34, 36, and 38 are preferably applied by well known surgical staplers (not shown) which are provided in the size-specific kit containing the tissue cutting template and die, the size of the staplers varying with the size of the patient's annulus. Stapling the tissue has been found to provide a quick, accurate method of securing the tissue together permanently. The staplers are preferably configured to match the tissue thickness. Other means for securing the inner and outer walls together, such as suturing, could also be employed instead of stapling.

The inner walls 20 of the segments 28, 30, and 32, which are fixed at their lower edges to the outer wall 22 of the valve by the staple segments 34, 36, and 38, form the cusps of the assembled valve. The provision of the scallops 16 on the top of the inner wall 20 advantageously ensures the availability of a greater amount of tissue along the free edges of the leaflets for better coaption between the commissures of the valve.

After adding the two sets of staple rows 24, 25, 26, 27, 34, 36, and 36 to the tissue rectangle 10, the valve maker joins each of the end tissue edges 15a and 15b which are parallel to the staple rows 25 and 27. Other techniques, such as suturing, could, of course, also be used to secure the end edges of the tissue 10 together.

Figure 8:
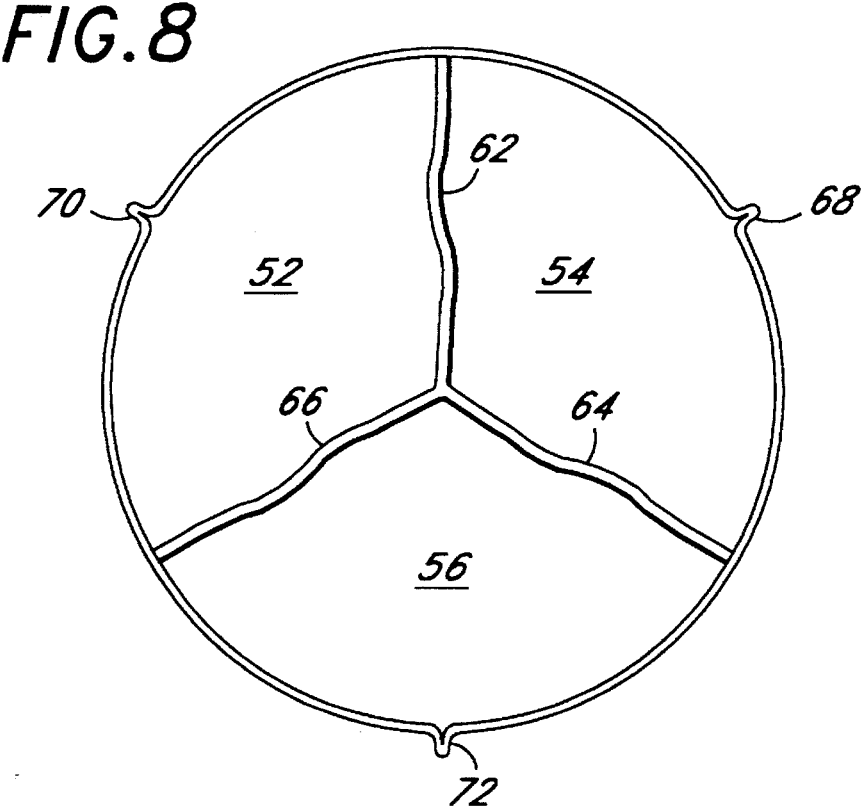
FIG. 8 is an elevation view of the valve leaflets of the present invention when in the closed position.
Figure 9:
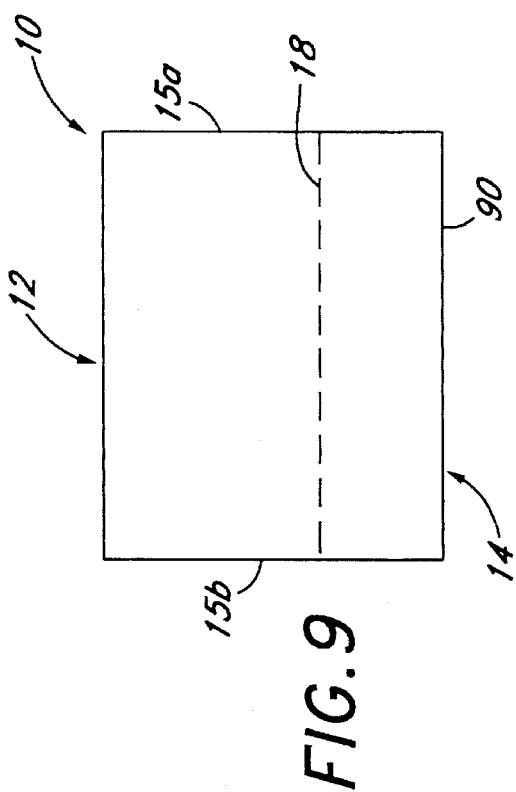
FIG. 9 is a top view of a section of tissue used to construct a second embodiment of the heart valve of the present invention.
Figure 10:
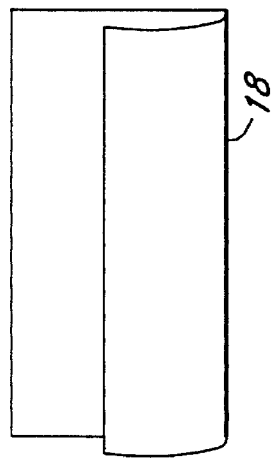
FIG. 10 is a top view of the tissue section depicted in FIG. 9 after it has been folded.
Figure 11:
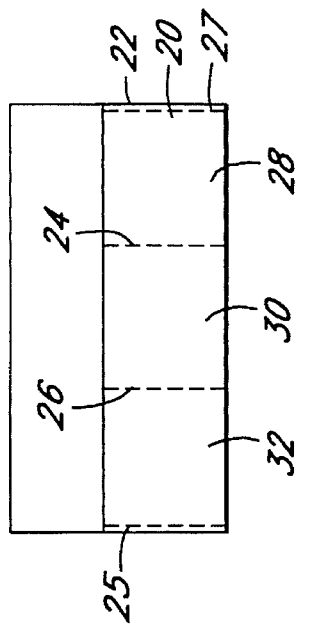
FIG. 11 is a perspective view of the tissue section depicted in FIG. 10 illustrating the placement of the first row of staples in an alternate embodiment of the present invention.
Figure 12:
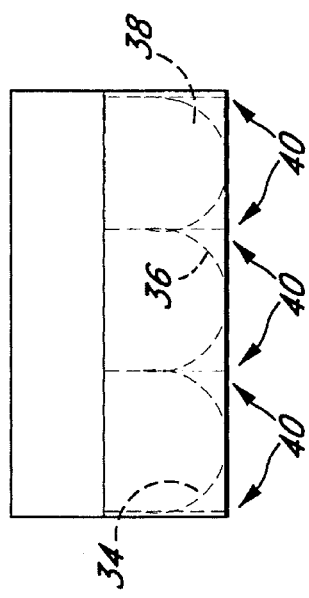
FIG. 12 is a top view of the tissue section depicted in FIG. 11 illustrating the placement of the second row of staples in curvilinear geometry.

The resulting valve 50, illustrated in FIGS. 5 and 8, contains three leaflets 52, 54, and 56, which are the inner walls of the segments 28, 30, and 32. An important feature of the present invention is the provision of the portion of the outer wall 22 distal to the top of the inner wall 20 as an outflow tract 60, which can be tailored to the patient's vascular anatomy. This allows the surgeon to cut portions of this outflow tract 60 to precisely tailor it to the anatomy of the patient before implanting the valve in the patient.

As can be seen in FIG. 8, the valve leaflets 52, 54, and 56 coapt at edges 62, 64, and 66. The outer wall of the valve of the present invention is advantageously tucked opposite the top or distal end of the inner wall at a plurality of locations 68, 70, and 72 midway along each of the arcs defined by the edges of the leaflets 52, 54, and 56 and formed by the valve annulus 6. This important feature reduces the circumference of the outer wall, thus leaving a greater length of tissue on the inner wall than on the outer wall. This achieves the object of preventing the leaflets from adhering to the outer wall of the valve by surface tension and consequently preventing the valve's closure. By pinching the wall at these locations, the top portion of each of the leaflets is displaced from the outer wall, thus preventing adhesion. The outer wall is preferably tucked or pinched by the surgeon and then a suture or, most preferably, a staple, is emplaced to make the pinch a permanent feature of the valve at the locations shown at 68, 70, and 72.

In another embodiment of the present invention, illustrated in FIG. 7, the leaflets are prevented from adhering to the outer wall of the valve by the use of a girdle 74 placed around the midsection of the valve. The girdle is preferably fashioned from synthetic material, cloth, or is cloth-covered. The girdle is placed and secured around the midsection of the valve 50, constricting it to form valve sinuses 76. The sinuses 76 provide sufficient curvature to the outer wall of the valve to prevent the leaflets 52, 54, and 56 from adhering to the wall.

Following the emplacement of either the pinching staples or the girdle in the valve, the surgeon implants the completed valve into the patient, preferably by suturing the proximal end of the valve along a line within 1 mm of the fold 18 into the heart of the patient at location 78, as shown in FIG. 6. The surgeon then cuts the distal end of the valve 50 to conform to the patient's vascular anatomy and finally sutures the distal end of the valve into the patient's vein or artery, as, for example, the patient's pulmonary artery at location 80.

FIGS. 9–12 illustrate a second embodiment of the present invention, in which corresponding numbers denote like parts. The surgeon or technician begins the fabrication of the valve of the second embodiment by cutting a tissue rectangle 10 having a straight lower edge 90. The subsequent steps in the fabrication and implantation of the valve are identical to those employed in the first embodiment and described in detail above.

The valve of the present invention is very well suited for the low pressure-differential environment characteristic of the pulmonary valve of the patient; however, it could be equally well used in the aortic position or any other position in which an unstented three-leaflet valve would be satisfactory.

It can thus be seen that the valve of the present invention is easily manufactured by a vascular surgeon or technician in an operating-room environment. The size-specific kits containing staplers and cutting dies of the invention also allow the valve of the present invention to be precisely fabricated in a short amount of time.

While embodiments and applications of this invention have been shown and described, it should be apparent that the present disclosure of the preferred embodiment may be changed by a person skilled in the art without departing from the scope of the appended claims.

What is claimed is:

1. A stentless prosthetic heart valve formed from tissue removed from a patient during open heart surgery, said heart valve comprising:

a single piece of autologous tissue substantially entirely forming said heart valve, inner and outer layers of said tissue having a common fold, said layers secured to each other along two lines extending distally from said fold to form three segments of tissue, said folded tissue having opposing ends, said opposing ends being parallel to said two distally extending lines, said opposing ends being joined together to form an annular, self-supporting heart valve in which the three segments of inner tissue form three coapting valve cusps.

2. A stentless prosthetic heart valve formed from tissue removed from a patient during open heart surgery, said heart valve comprising:

a single piece of autologous tissue substantially entirely forming said heart valve, inner and outer layers of said tissue having a common fold, said layers secured to each other along two lines extending distally from said fold to form three segments of tissue, each segment having opposing corners at said fold, said inner and outer layers secured together along an arc formed in each segment, said arc sealing the corners of said segments of tissue from bloodflow through said valve to prevent stagnation of blood in said valve during the operation thereof, said folded tissue having opposing ends, said opposing ends being parallel to said two distally extending lines, said opposing ends being joined together to form an annular, self-supporting heart valve in which the three segments of inner tissue form three coapting valve cusps.

3. A stentless prosthetic heart valve formed from tissue removed from a patient during open heart surgery, said heart valve comprising:

a single piece of autologous tissue substantially entirely forming said heart valve, inner and outer layers of said tissue having a common fold, the upper end of said inner layer having a straight edge, said layers secured to each other along two lines extending distally from said fold to form three segments of tissue, said folded tissue having opposing ends, said opposing ends being parallel to said two distally extending lines, said opposing ends being joined together to form an annular, self-supporting heart valve in which the three segments of inner tissue form three coapting valve cusps.

4. A stentless prosthetic heart valve formed from tissue removed from a patient during open heart surgery, said heart valve comprising:

a single piece of autologous tissue substantially entirely forming said heart valve, inner and outer layers of said tissue having a common fold, a distal end of said tissue being cut into a scalloped shape, said inner layer including an upper edge having said distal end scalloped shape and an outer layer of tissue, said layers secured to each other along two lines extending distally from said fold to form three segments of tissue, said folded tissue having opposing ends, said opposing ends being parallel to said two distally extending lines, said opposing ends being joined together to form an annular, self-supporting heart valve in which the three segments of inner tissue form three coapting valve cusps, whereby said scalloped shape of said upper edge of the inner layer provides greater coaptive surface area for said valve cusps.

5. A stentless prosthetic heart valve formed from tissue removed from a patient during open heart surgery, said heart valve comprising:

a single piece of autologous tissue substantially entirely forming said heart valve, inner and outer layers of said tissue having a common fold, said layers secured to each other along two lines extending distally from said fold to form three segments of tissue, said folded tissue having opposing ends, said opposing ends being parallel to said two distally extending lines, said opposing ends being joined together to form an annular, self-supporting heart valve in which the three segments of inner tissue form three coapting valve cusps, said outer layer of tissue pinched at three locations opposite the distal end of said inner layer of tissue at a midpoint of each segment of tissue to prevent said valve cusps from adhering to said outer layer of tissue during operation of said valve.

6. The prosthetic heart valve of claim 5 wherein said outer layer of tissue is pinched by emplacement of a single staple at the midpoint of each segment of tissue opposite the distal end of said inner layer of tissue.

7. A stentless prosthetic heart valve formed from tissue removed from a patient during open heart surgery, said heart valve comprising:

a single piece of autologous tissue substantially entirely forming said heart valve, inner and outer layers of said tissue having a common fold, said layers secured to each other along two lines extending distally from said fold to form three segments of tissue, said folded tissue having opposing ends, said opposing ends being parallel to said two distally extending lines, said opposing ends being joined together to form an annular, self-supporting heart valve in which the three segments of inner tissue form three coapting valve cusps, said prosthetic heart valve including a prosthetic cloth or cloth-covered girdle placed around and constricting the midsection of said valve, said girdle preventing said cusps from adhering to said outer layer of tissue during operation of said valve.

8. A stentless prosthetic heart valve formed from tissue removed from a patient during open heart surgery, said heart valve comprising:

a single piece of autologous tissue substantially entirely forming said heart valve, inner and outer layers of said tissue having a common fold, said layers secured to each other along two lines extending distally from said fold to form three segments of tissue, said outer layer of tissue extending distally from the distal end of said inner layer to form an outflow tract, said outflow tract selectively cut to match said patient's vascular anatomy, said folded tissue having opposing ends, said opposing ends being parallel to said two distally extending lines, said opposing ends being joined together form an annular, self-supporting heart valve in which the three segments of inner tissue form three coapting valve cusps.

9. A stentless prosthetic heart valve formed from removed from a patient during open heart surgery, said heart valve comprising:

a single piece of autologous tissue substantially entirely forming said heart valve, said tissue briefly immersed in a solution containing at least 0.6% glutaraldehyde, inner and outer layers of said tissue having a common fold, said layers secured to each other along two lines extending distally from said fold to form three segments of tissue, said folded tissue having opposing ends, said opposing ends being parallel to said two distally extending lines, said opposing ends being joined together to form an annular, self-supporting heart valve in which the three segments of inner tissue form three coapting valve cusps.

10. A cardiac valve, comprising:

a self-supporting annular body formed substantially entirely from a single piece of autologous pericardium tissue, said tissue having distal and proximal ends, said distal end of said tissue cut into a plurality of scalloped portions, said tissue folded at a fold to form inner and outer layers of tissue, said inner and outer layers of tissue stapled together at a first set of staples along a plurality of lines extending distally from said fold, said inner and outer layers stapled at a second set of staples in a plurality of arcs at said fold, said inner layer of tissue forming a plurality of valve cusps coapting with one another, said second set of staples preventing areas of bloodflow stagnation from forming during operation of said valve, and said scalloped portions providing improved coaption between said valve leaflets.

11. A cardiac valve, comprising:

a single piece of autologous tissue substantially entirely forming said valve, a self-supporting annular body of said tissue having distal and proximal ends, said tissue folded at a fold location to form a plurality of layers of tissue, said layers of tissue secured together along a plurality of lines extending distally from said fold location of said valve.

12. The cardiac valve of claim 11, wherein said layers are secured together by staples.

13. The cardiac valve of claim 11, wherein said layers are secured together by sutures.

14. The cardiac valve of claim 11, wherein said layers are secured together along a plurality of arcs at said fold location of said valve.

15. The cardiac valve of claim 11, wherein said proximal end of said tissue is cut into a plurality of scalloped portions.

16. The cardiac valve of claim 11, wherein a layer of said tissue is tucked at a plurality of locations around said annular body of tissue to prevent said layers from adhering to each other during operation of said valve.

17. The cardiac valve of claim 16, wherein a layer of said tissue is tucked midway between each of said lines securing said tissue opposite the distal end of the innermost of said layers.

18. The cardiac valve of claim 16, wherein a layer of said tissue is tucked by emplacement of a suture in said outer layer opposite the distal end of the innermost of said layers.

19. The cardiac valve of claim 16, wherein a layer of said tissue is tucked by emplacement of a staple in said outer layer opposite the distal end of the innermost of said layers.

20. The cardiac valve of claim 11, wherein said proximal end of said tissue has a straight edge.

21. The cardiac valve of claim 11, further comprising:

a girdle placed around the outside of the middle section of said valve, said girdle constricting the middle section of said valve to form a sinus, said girdle thereby preventing said layers of said tissue from adhering during operation of said valve.

22. The cardiac valve of claim 11 wherein said tissue is immersed in a solution containing glutaraldehyde.

23. The cardiac valve of claim 11 wherein said tissue is autologous pericardium.

24. The cardiac valve of claim 11 wherein said tissue is autologous fascia lata.

25. A cardiac valve, comprising:

a self-supporting annular body consisting of substantially a single piece of autologous tissue, said tissue having a distal end and a proximal end, said distal end cut along a plurality of scalloped sections, said tissue folded at a location distally from said proximal end to form inner and outer layers, said inner and outer layers of tissue secured along a plurality of lines extending distally from said folded location of said valve to the top of said inner layer, said inner and outer layers of tissue secured at the fold forming said inner and outer layers along a plurality of arcs, each of said arcs tangent at its midpoint to said fold, said outer layer pinched at a plurality of locations opposite the distal end of said inner layer to prevent said inner and said outer layers from adhering to each other during the operation of said valve.

26. A stentless prosthetic heart valve formed from tissue removed from a patient during open heart surgery, said valve comprising a single piece of autologous tissue substantially entirely forming said valve, said valve having an annular configuration in which said tissue has been folded into two layers and said layers have been secured to one another into three outer and inner segments, the inner segments of said annular configuration comprising three coapting valve cusps.

27. A stentless prosthetic heart valve, comprising:

a self-supporting annular body consisting substantially of a single piece of autologous pericardial tissue, said tissue having inner and outer layers, said tissue having a common fold, said layers secured to each other along two lines extending distally from said fold to form three segments of tissue, said folded tissue having opposing ends, said opposing ends being parallel to said two distally extending lines, said opposing ends being joined together to form the annular body of the heart valve in which the three segments of inner tissue form three coapting valve cusps.

28. A stentless prosthetic heart valve, comprising:

a self-supporting annular body consisting substantially of a single piece of autologous pericardial tissue, said tissue having inner and outer layers, said tissue having a common fold, said inner and outer layers of tissue stapled together along a plurality of lines extending distally from said fold to form three segments of tissue, said folded tissue having opposing ends, said opposing ends being parallel to said plurality of distally extending lines, said opposing ends being joined together to form the annular body of the heart valve in which the three segments of inner tissue form three coapting valve cusps.

29. The heart valve of claim 26 wherein said tissue is autologous pericardium.

30. The heart valve of claim 26, wherein said tissue is autologous fascia lata.

* * * * *